United States Patent [19]

Anderhub

[11] Patent Number: 5,215,540
[45] Date of Patent: Jun. 1, 1993

[54] RIGHT CORONARY CATHETER

[75] Inventor: Otto E. Anderhub, Miami, Fla.

[73] Assignee: St. Jude Medical, Inc., St. Paul, Minn. ; a part interest

[21] Appl. No.: 828,420

[22] Filed: Jan. 31, 1992

[51] Int. Cl.$^5$ ............................................. A61M 25/00
[52] U.S. Cl. ...................... 604/281; 604/264
[58] Field of Search ................ 604/280, 281, 264, 284

[56] References Cited

U.S. PATENT DOCUMENTS

| Re. 29,343 | 8/1977 | Amplatz . | |
|---|---|---|---|
| 4,033,331 | 7/1977 | Guss et al. . | |
| 4,117,836 | 10/1978 | Erikson | 604/281 |
| 4,215,703 | 8/1980 | Willson . | |
| 4,563,181 | 7/1986 | Wijayarathna et al. . | |
| 4,735,620 | 4/1988 | Ruiz . | |
| 4,781,682 | 11/1988 | Patel . | |
| 4,784,639 | 11/1988 | Patel | 604/280 |
| 4,838,879 | 6/1989 | Tanabe et al. . | |
| 4,846,814 | 7/1989 | Ruiz . | |
| 4,883,058 | 11/1989 | Ruiz | 604/281 |
| 4,886,506 | 12/1989 | Lovgren et al. . | |
| 4,935,017 | 6/1990 | Sylvanowicz . | |
| 5,016,640 | 5/1991 | Ruiz . | |
| 5,045,072 | 9/1991 | Castillo et al. . | |
| 5,058,595 | 10/1991 | Kern | 604/281 |

FOREIGN PATENT DOCUMENTS 930636  7/1973  Canada .

OTHER PUBLICATIONS

Cordis Corp., "Ducor" catheter brochure, 1974.
Arani, D. T., "A New Catheter For Angioplasty Of The Right Coronary Artery And Aorto-Coronary Bypass Grafts", *Catherization and Cardiovascular Diagnosis*, vol. 11, pp. 647–653 (1985).
USCI Angioplasty Products Price List, 1988, p. 29, illustrating Arani Right Coronary Catheters.
Arani, D. T., et al., "Double Loop Guiding Catheter: A Primary Catheter For Antioplasty Of The Right Coronary Artery", *Catherization and Cardiovascular Diagnosis*, vol. 15, pp. 125–131 (1988).

*Primary Examiner*—Paul J. Hirsch
*Attorney, Agent, or Firm*—Leydig, Voit & Mayer

[57] ABSTRACT

A right coronary catheter for use in selective coronary arteriography using a femoral artery approach. The catheter is preformed to permit insertion of the catheter tip into the orifice of the right coronary artery without substantial rotation of the catheter body. In addition, the configuration of the catheter renders it adaptable to most coronary anatomies thereby avoiding the need to estimate and preselect a catheter geometry for each individual patient variation.

4 Claims, 7 Drawing Sheets

RIGHT CORONARY CATHETER

FIELD OF THE INVENTION

The present invention relates generally to coronary catheters and more particularly to a new and useful coronary catheter for selective coronary arteriography of the human right coronary artery using a femoral artery approach.

BACKGROUND OF THE INVENTION

The use of coronary catheters in selective coronary arteriography procedures for the identification and evaluation of arterial blockage in major coronary arteries is well known. This evaluation is carried out by means of injection of a radiopaque tracer media through a flexible catheter into a coronary artery and thereafter monitoring the fluid flow characteristics exhibited within that artery by means of X-ray imagery as the radiopaque tracer is transported with the blood through the artery under evaluation.

As will be readily recognized, the introduction of both the catheter and the radiopaque media to the vessel under evaluation must be carried out without trauma to either the heart muscle itself or the blood vessels within the heart. In order to gain access to the coronary arteries without damaging the area to be studied, a hollow flexible catheter is introduced into a major blood vessel in an area of the body remote from the heart and guided to the coronary artery to be studied. The radiopaque tracer is then injected through the catheter and into the artery under evaluation.

In carrying out coronary arteriography of a right coronary artery, a percutaneous entry is typically made at the femoral artery. Catheters used in conjunction with a femoral approach include the Amplatz and the Judkins configurations (FIGS. 6 and 7, respectively) wherein the catheter tip is oriented at substantially a 90° angle to the adjacent section of the catheter body. In a femoral artery approach procedure, a guidewire is generally threaded to a point above the aortic bifurcation. The catheter is inserted over the guidewire and the catheter and guidewire are eased up the aorta until the tip of the guidewire reaches the distal portion of the coronary arch. At this stage, the guidewire is generally removed and the flexible catheter is advanced over the coronary arch and manipulated to engage the tip of the catheter with the orifice of the right coronary artery.

Since the catheter in a femoral approach procedure must be advanced through the aortic arch and inserted into the orifice of the coronary artery, the catheter must cooperate with the anatomical configuration of the arch and orifice. Accordingly, catheters have typically been fabricated from low temperature thermoplastic materials such as polyurethane which have inherent pliability and elasticity. In addition, catheters have typically been preshaped to conform to the arch and coronary artery anatomies generally encountered, with different sizes being available for patients with anatomical variations in the aortic root arising from differences in age, weight, disease, and other physical characteristics.

Moreover, the combined need to easily pass the catheter over the coronary arch while at the same time having the catheter conform to the anatomy of the coronary arch and artery orifice once in place has heretofore presented significant difficulty with respect to catheterization of the right coronary artery. The right coronary artery is situated on the outer perimeter of the ascending aorta past the coronary arch, thereby preventing easy insertion of the catheter tip as it travels along the natural curve of the arch.

Prior to the present invention, the solution to this difficulty has been to equip the catheter with a tip portion bent at approximately 90° to the adjacent body portion of the catheter. The catheter was then advanced through the coronary arch with the tip portion directed towards the axis of curvature of the arch (i.e., away from the right coronary artery orifice), thereby facilitating passage through the arch. After the tip portion had passed substantially over the coronary arch, the entire catheter was rotated approximately 180° to bring the catheter tip into contact with the orifice of the right coronary artery. Performing this rotation, however, requires considerable skill and gives rise to a serious potential for vessel trauma as the tip of the catheter sweeps, sometimes with a whipping action, into place.

Despite the existence of right coronary catheters for use in selective coronary arteriography which may be inserted directly into the orifice of the right coronary artery by means of a brachial approach procedure, or which may be rotated into position after being guided over the aortic arch in a femoral artery approach procedure, there remains a need for a right coronary catheter which may be inserted directly into the orifice of the right coronary artery by means of a femoral artery approach procedure without rotation of the catheter while in the coronary arch. There is also a need of a right coronary catheter which is of a substantially universal size which can be used with most patients.

OBJECTS AND SUMMARY OF THE INVENTION

The primary object of the present invention is to provide a new and useful right coronary catheter capable of being inserted into the orifice of the right coronary artery with no rotation after being guided through the aortic arch by means of a femoral approach procedure. It is a further object of the invention to provide a right coronary catheter having a geometry which renders it suitable for use in most patients regardless of the anatomical configuration of their coronary arch and artery orifice.

Accordingly, the present invention provides a flexible preformed right coronary catheter having a primary curve defining a catheter tip, a secondary curve, a substantially straight central body portion and a substantially straight rear body portion. The angle formed by the primary curve in the present invention is significantly less than the 90° angle utilized in some prior art devices. In addition, the present invention generally avoids the need to preselect a catheter geometry conforming to each individual patient's cardiac anatomy.

While the present invention will be described and disclosed in connection with certain preferred embodiments, it is not intended to limit the invention to those specific embodiments. Rather, it is the applicant's intention to cover all such alternative embodiments and modifications as fall within the spirit and scope of the appended claims.

DETAILED DESCRIPTION OF THE PREFERRED EMBODIMENT

Figure 1:
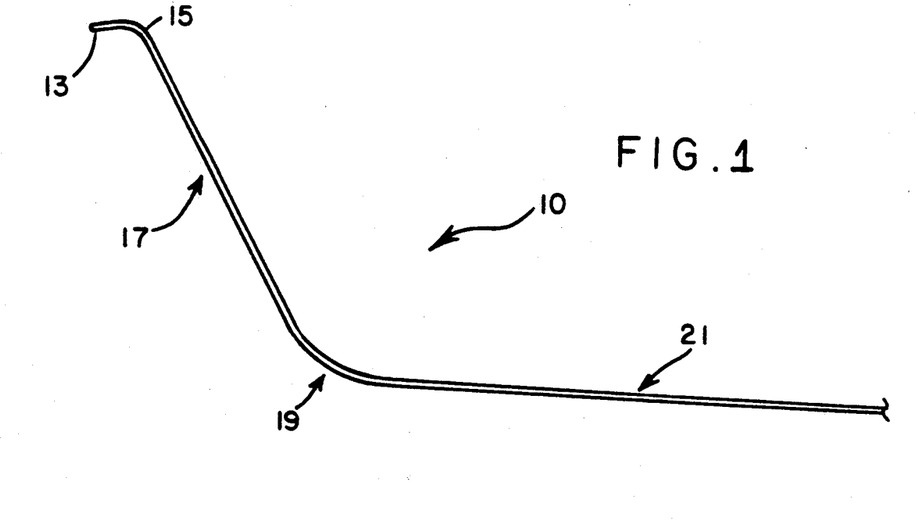
FIG. 1 is a side view of a right coronary catheter according to the present invention.

Turning now to the drawings, a right coronary catheter 10 according to the present invention is shown generally in FIG. 1. The catheter 10 includes a tip portion 13, a primary curve 15, a substantially straight central body portion 17, a secondary curve 19, and a substantially straight rear body portion 21. As will be recognized by those skilled in the art, the catheter 10 is a hollow tube and is preferably fabricated from a low temperature thermoplastic such as polyurethane or a like material having inherent properties of pliability and elasticity, thereby permitting substantial bending of the catheter 10 with no resultant permanent deformation.

Figure 2:
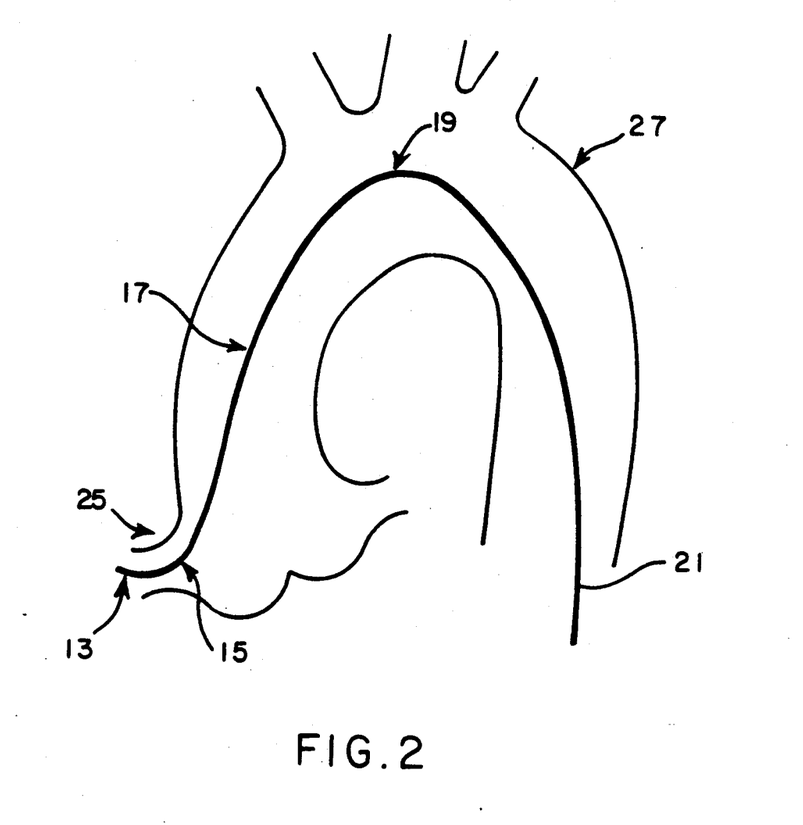
FIG. 2 is a cross sectional view of a human coronary arch with the right coronary catheter of FIG. 1 disposed in working orientation.

The insertion of the tip 13 of catheter 10 into the orifice of right coronary artery 25 is shown in FIG. 2. The preformed shape of catheter 10 aids in its safe advancement over the coronary arch 27 and into the orifice of the right coronary artery 25. As will be appreciated from examination of FIG. 2, an appropriate preformed structure is essential to avoid undue interference with surrounding tissue as the catheter 10 is passed over the coronary arch 27 while nonetheless permitting direct engagement of catheter tip 13 into the orifice of the right coronary artery 25 once the catheter 10 is in place.

Figure 3:
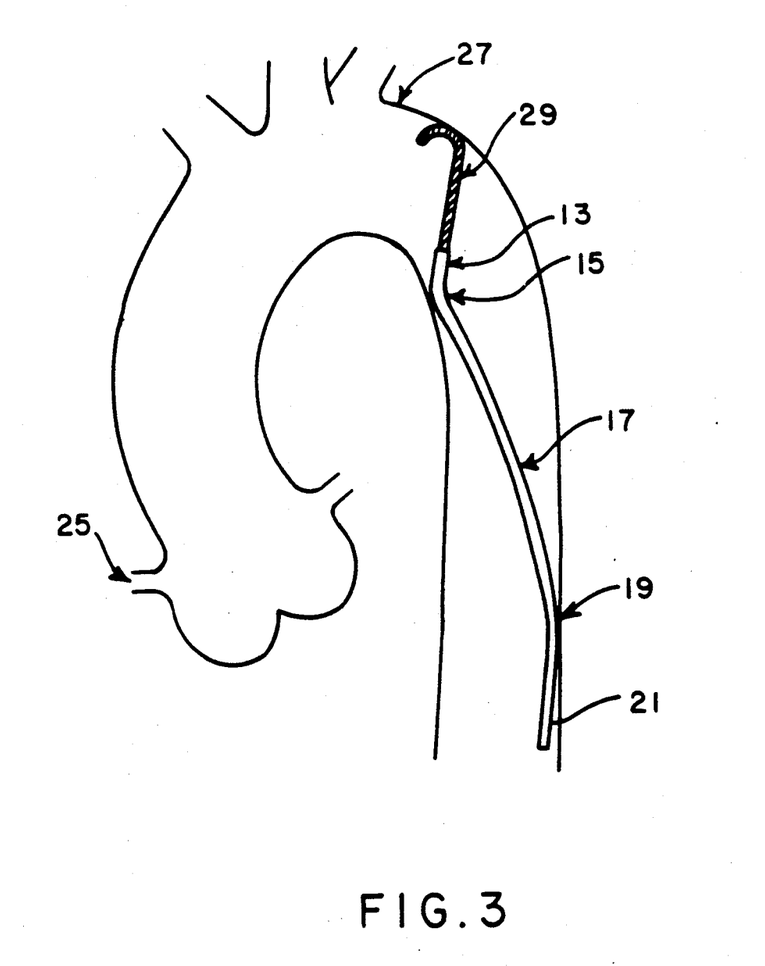
FIG. 3 is a cross sectional view of a human coronary arch with the right coronary catheter of FIG. i disposed over a guidewire prior to advancement over the coronary arch.
Figure 4A:
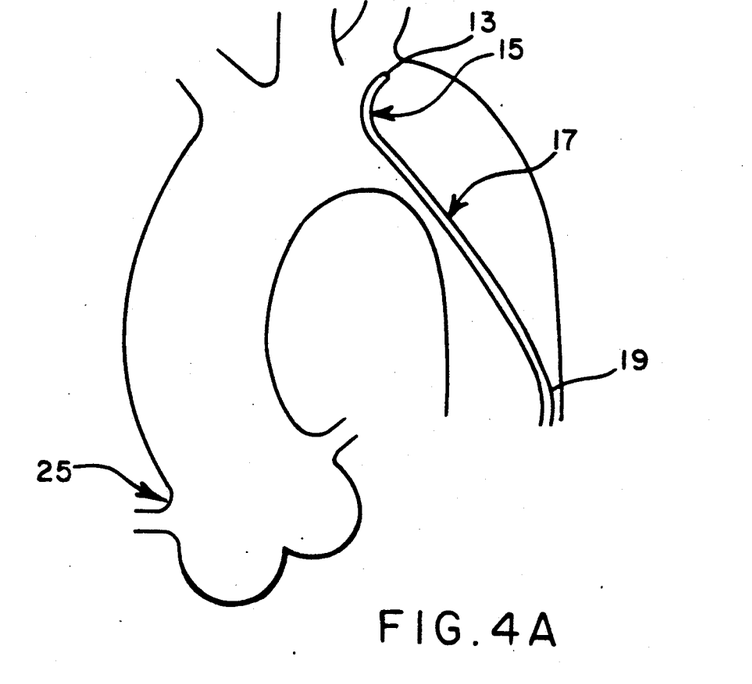
FIGS. 4A–4D are sequential cross sectional views of a human coronary arch showing the catheter of FIG. I in intermediate stages of advancement between the position shown in FIG. 3 and the position shown in FIG. 2.
Figure 4B:
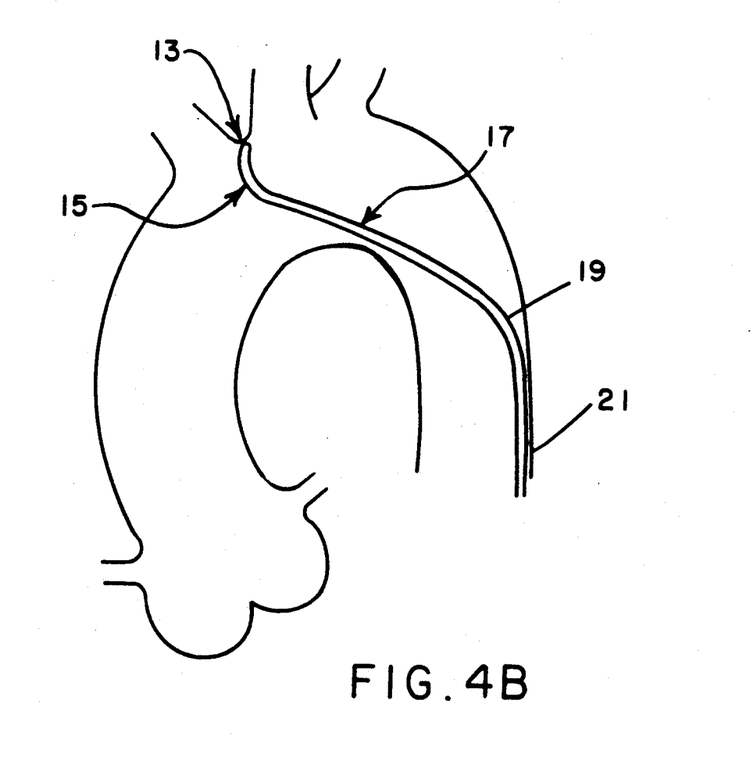
Figure 4C:
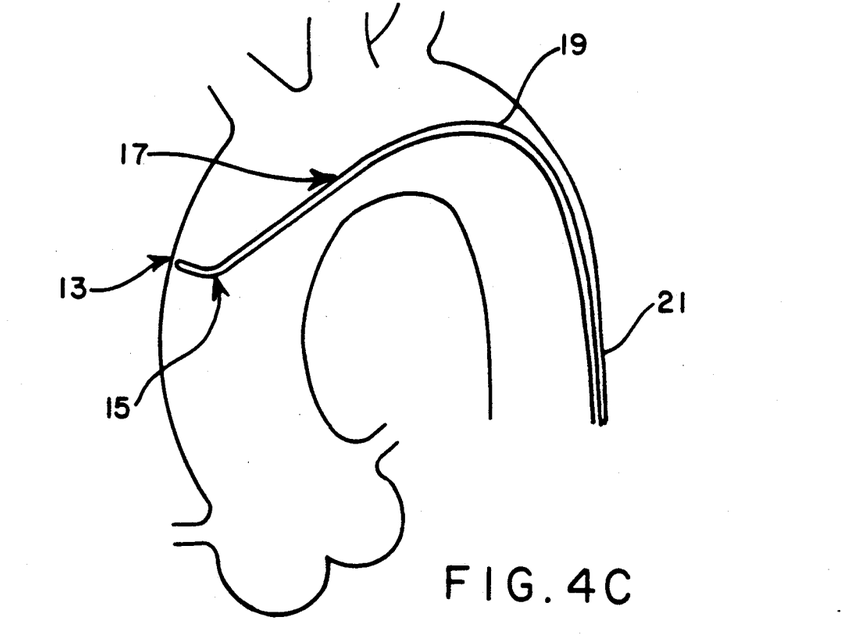
Figure 4D:
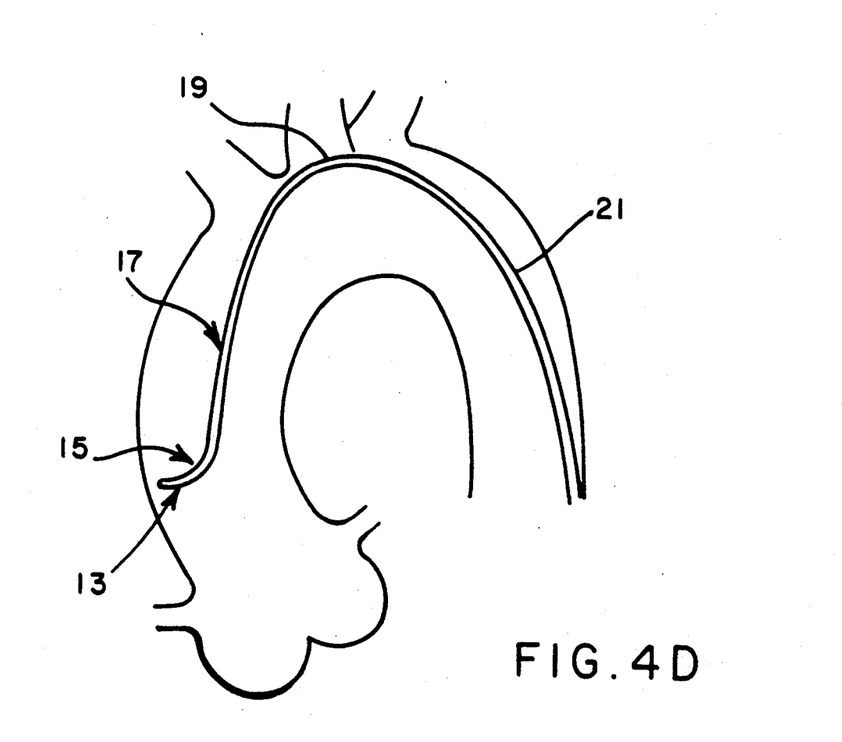

The right coronary catheter 10 of the present invention utilizes a set of two curves 15 and 19 to interconnect the catheter tip 13 and the substantially straight catheter body portions 17 and 21. It is the angular relation between catheter portions defined by primary curve 15 and secondary curve 19 which permits the insertion of the catheter tip 13 into the right coronary artery 25 substantially without rotation while avoiding undue interference with the vessel walls. The advancement of the right coronary catheter 10 of the present invention over the coronary arch 27 is shown in FIG. 3 and FIGS. 4A-4D. In FIG. 3, the right coronary catheter is disposed below the apex of the coronary arch 27 with the guidewire 29 still in place. As seen, the effect of the guidewire 29 is to substantially straighten the catheter. Upon reaching the position of FIG. 3, the guidewire 29 may be either removed or advanced further as required to maneuver the catheter over the coronary arch 27. FIGS. 4A-4D show the stages of advancement which the right coronary catheter 10 of the present invention will undergo as it advances along the coronary arch 27 and ultimately engages the orifice of the right coronary artery 25 as shown in FIG. 2. Specifically, FIG. 4A shows the position of the catheter 10 of the present invention after the guidewire 29 has been removed and advancement over the coronary arch 27 has been initiated. FIG. 4D shows the disposition of the catheter 10 of the present invention after advancement over the coronary arch 27 is substantially complete and immediately prior to engagement between the catheter tip portion 13 and the orifice of the right coronary artery 25 as shown in FIG. 2. FIGS. 4B and 4C show the position of the catheter 10 at intermediate stages of advancement over the coronary arch 27. As will be appreciated, the geometric configuration defined by curves 15 and 19 and straight portions 17 and 21 permits the catheter to adapt to the varying curvature of the coronary arch 27 as travel proceeds from the initial position below the arch 27 as shown in FIG. 3 to the position of final engagement with the right coronary artery 25 as shown in FIG. 2.

Figure 5:
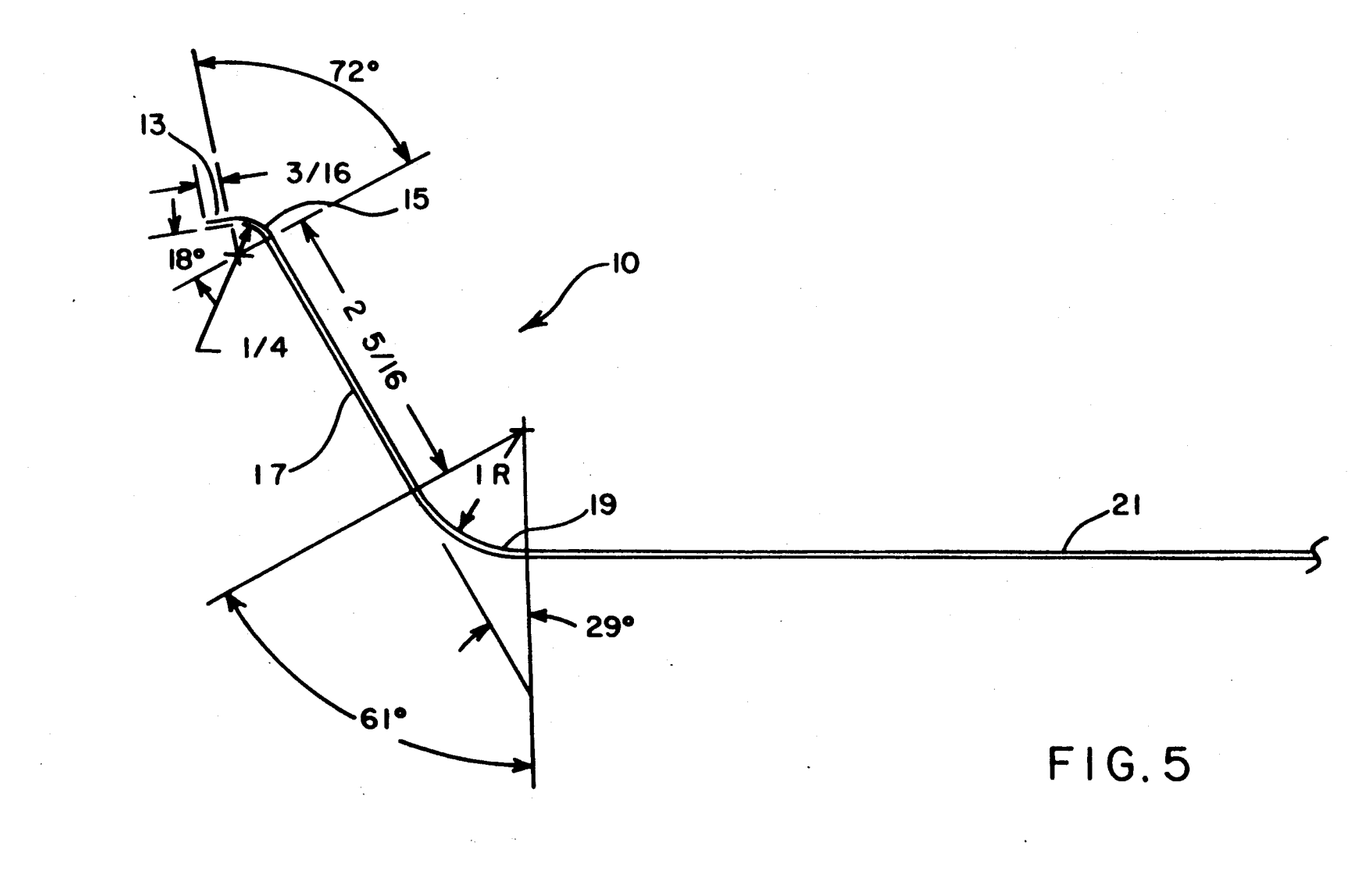
FIG. 5 is a specific geometric embodiment of the right coronary catheter of FIG. 1.
Figure 6:
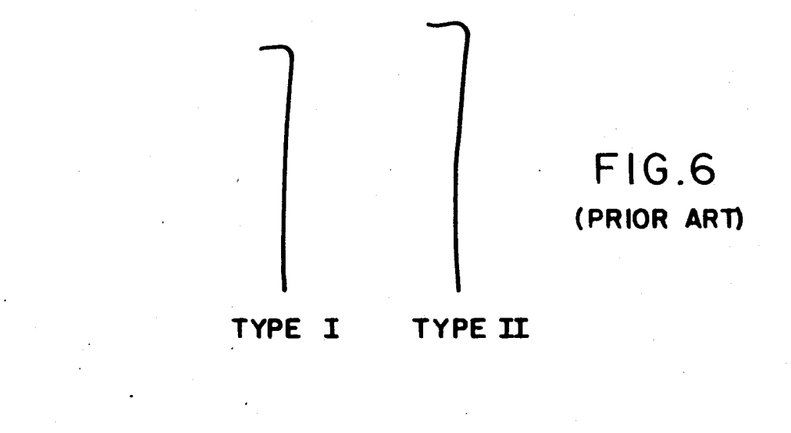
FIG. 6 illustrates two sizes of prior art right coronary catheter tips used in the Amplatz technique.
Figure 7:
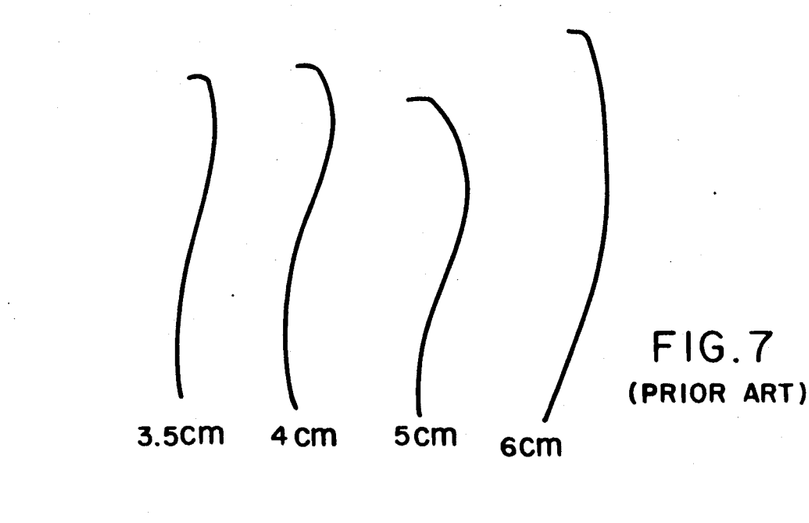
FIG. 7 illustrates four sizes of prior art right coronary catheter tips used in the Judkins technique.

While the invention is in no way intended to be limited, one specific geometric configuration of the present invention is shown in FIG. 5. In this embodiment, the angle between the tip 13 and the central body portion is about 72° while that between the central body portion and the rear body portion is about 61°. The length of the central body portion 17 in the embodiment shown extending between these two curves is 2-5/16 inches. The combination of these angles and central body portion length has been found to permit the catheter 10 to be advanced through the aorta in an efficient manner and to adapt to most anatomical variations in the size and configuration of the human coronary arch and right coronary artery. With such a configuration the present invention differs from that of some prior art femoral artery approach right coronary catheters wherein the tip of the catheters are disposed at an angle of about 90° or greater to the adjacent portion of the catheter body. Such prior art catheters are shown for reference purposes in FIGS. 6 and 7. Two sizes of Amplatz geometry catheters are shown in FIG. 6 while four sizes of Judkins geometry devices are shown in FIG. 7.

As seen, the prior art provides for variation in catheter size based on the predicted anatomical configuration of each patient's coronary arch 27 and right coronary artery 25. Thus, before catheterization may be performed, the user must first select the proper catheter size as estimated based on factors such as the patient's age, weight and disease. By contrast, the use of secondary curve 19 in conjunction with two substantially straight body portions 17 and 21 in the flexible catheter 10 of the present invention avoids this preselection requirement by virtue of the fact that secondary curve 19 and substantially straight body portions 17 and 21 will naturally conform, by means of the elastic properties of the catheter material, to substantially all coronary arch configurations.

Figure 8A:
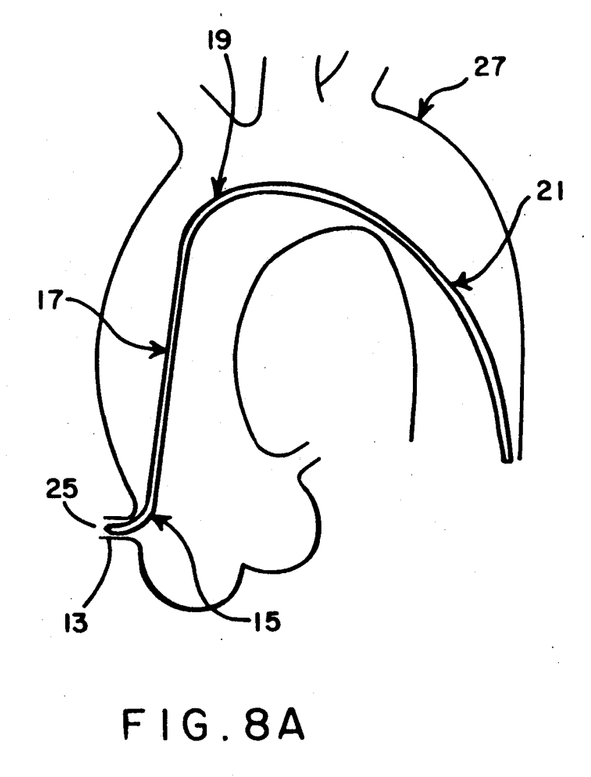
FIG. 8A is a cross-sectional view of a human coronary arch showing the right coronary catheter of FIG. 1 disposed in a normal aorta.
Figure 8B:
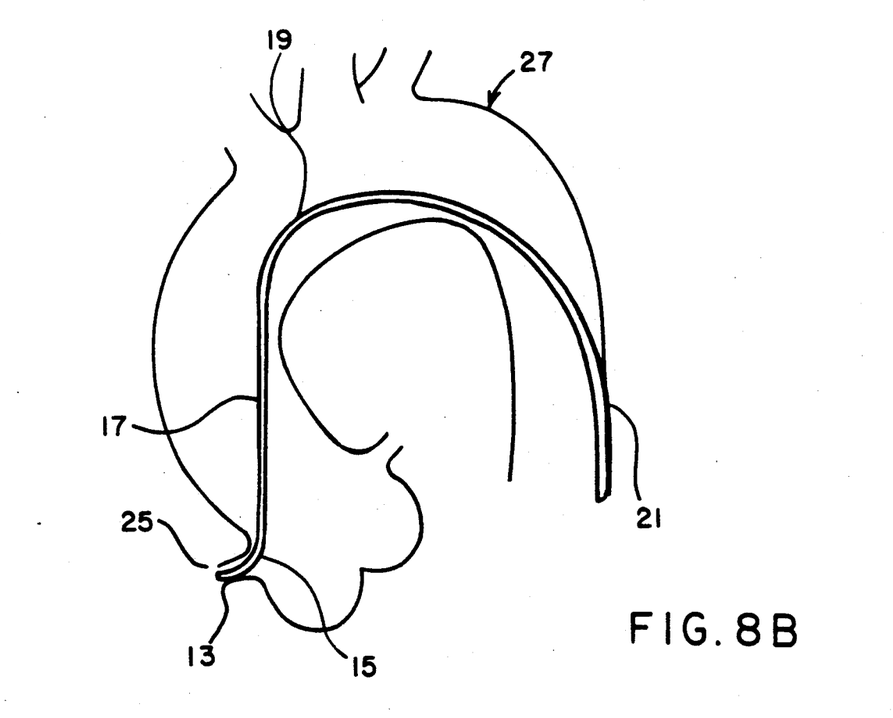
FIG. 8B is a cross-sectional view of a human coronary arch showing the right coronary catheter of FIG. 1 disposed in an unfolded aorta.
Figure 8C:
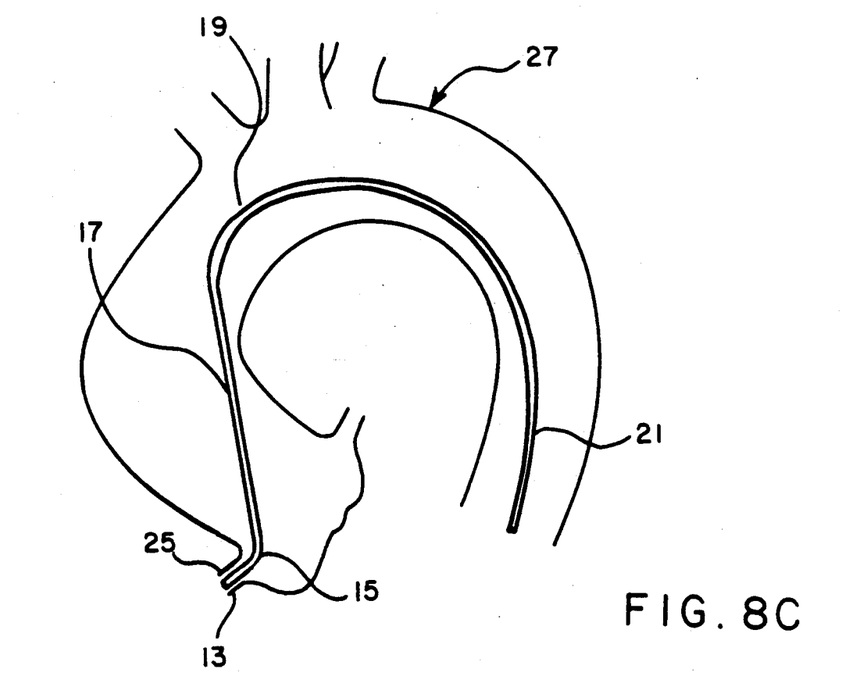
FIG. 8C is a cross sectional view of a human coronary arch showing the right coronary catheter of FIG. 1 disposed in a poststenotic aorta.

This ability to conform to a variety of aortic anatomies is shown in FIGS. 8A, 8B and 8C. FIG. 8A shows a right coronary catheter 10 according to the present invention disposed within a normal aorta. FIG. 8B shows the catheter 10 of the present invention disposed within an unfolded aorta. Finally, FIG. 8C shows the catheter 10 of the present invention disposed within a poststenotic aorta. In each of these cases the catheter may be advanced as illustrated in the sequence illustrated in FIGS. 4A-4D and readily achieve the final, desired position shown in FIG. 2. Hence, a single size catheter 10 of the present invention is able to conform to substantially all aortic anatomies. This is in contrast to Amplatz geometry catheters of FIG. 6 in which at least two catheter sizes are necessary and the Judkins geometry devices of FIG. 7 which in practice require the user to select between four different sizes.

In operation, the user of the catheter 10 of the present invention will guide the catheter 10 via the femoral artery into the descending aorta and directly over the coronary arch 27 with the tip portion 13 at all times pointed towards the outer perimeter as illustrated in FIGS. 4A-4D. The catheter tip 13 will then be directly inserted or engaged into the right coronary artery 25 without turning 180° as required by prior art devices. Thereafter, a radiopaque tracer will be injected through the catheter 10 and into the right coronary artery 25 thereby permitting X-ray visualization of the vessel and blood flow within the right coronary artery 25.

I claim as my invention:

1. A preformed right coronary catheter for use in coronary arteriography of the human right coronary artery using a femoral artery approach, comprising a primary curve, a secondary curve, a tip portion, a substantially straight central body portion and a substantially straight rear body portion, said primary curve being disposed between said tip portion and said central body portion and defining a first angle therebetween of substantially less than 90°, said secondary curve being disposed between said central body portion and said rear body portion and defining a second angle therebetween of about 60°, this geometry of said catheter enabling direct engagement and insertion of said catheter tip into said right coronary artery by means of a femoral artery approach without the need for catheter rotation.

2. A preformed right coronary catheter according to claim 1 wherein said first angle is about 70°, and said substantially straight central body portion is about 2Δ long such that said catheter conforms to substantially all anatomical variations in the size and configuration of the human coronary arch and right coronary artery.

3. A preformed right coronary catheter according to claim 1 wherein said catheter is comprised of a low temperature thermoplastic.

4. A preformed right coronary catheter according to claim 3 wherein said low temperature thermoplastic is polyurethane.

* * * * *